(12) United States Patent
Smith et al.

(10) Patent No.: US 6,399,801 B1
(45) Date of Patent: Jun. 4, 2002

(54) DRY POWDER LITHIUM CARBOXYLATES

(75) Inventors: W. Novis Smith; Joel McCloskey, both of Philadelphia, PA (US)

(73) Assignee: Lithchem International, Anaheim, CA (US)

( * ) Notice: Subject to any disclaimer, the term of this patent is extended or adjusted under 35 U.S.C. 154(b) by 0 days.

(21) Appl. No.: 09/564,972

(22) Filed: May 4, 2000

(51) Int. Cl.[7] ................................................. C07C 51/00
(52) U.S. Cl. ....................................... 554/156; 562/512
(58) Field of Search ................................. 554/195, 178, 554/156; 562/552, 512; 106/156.24; 502/170; 508/523, 491, 486, 539

(56) References Cited

U.S. PATENT DOCUMENTS 5,595,965 A * 1/1997 Wiggins ...................... 508/491

* cited by examiner

*Primary Examiner*—Deborah D. Carr
(74) *Attorney, Agent, or Firm*—John Lezdey & Assoc

(57) ABSTRACT

The invention provides a process for preparing lithium carboxylates which can be used in the preparation of soaps, oils and greases. The process utilizes molten carboxylic acids in a reaction utilizing a minimum of water and provides a powdery product which does not need filtration.

9 Claims, No Drawings

DRY POWDER LITHIUM CARBOXYLATES

BACKGROUND OF THE INVENTION

1. Field of the Invention

The invention relates to the preparation of lubricating greases which can be used in the automotive and aerospace industry. More particularly, there is provided an improved method for preparing dry powder lithium carboxylates for use in lithium based greases.

2. Description of the Prior Art

Lithium soaps and complex soaps used as thickening agents for lubricating greases are generally prepared by reacting lithium hydroxide monohydrate or other lithium bases with aliphatic monocarboxylic and/or dicarboxylic acids which may be saturated or unsaturated, straight or branched chain, and may be hydroxy substituted. Preferably, these acids contain about 6 to 30 carbon atoms and more preferably, from about 6 to 18 carbon atoms. It has long been known that a grease comprising a lithium soap of hydrogenated castor oil, or the lithium soap of 12-hydroxy stearic acid provide greases with exceedingly high m mechanical stability and excellent water resistance.

In general, any of the conventional lubricating oils such as mineral, animal, vegetable or synthetic lubrication oils, may be employed as the grease base stock. These lubricating oils have a viscosity in the range of about 35 to 200 SSU at 210° F. Mixtures of lubricating oils may also be effectively utilized. The grease compositions will usually contain about 70 to 95 weight percent, preferably about 80 to 95 weight percent, based on the total grease of the lubricating oil base. The lithium soap content may range from about 5 to 30 weight percent, preferably about 8 to 20 weight percent based on the total soap composition.

The prior art lithium greases are prepared as follows. The 12-hydroxy stearic acid or hydrogenated castor oil is dissolved in lubricating oil while heating to about 125 to 175° F. at atmospheric pressure. Lithium hydroxide is dissolved in water and then added to this solution at about 180–190° F., in a stoichiometric amount for complete reaction saponification of the 12-hydroxy stearic acid and to provide a mixture of the lubrication oil and lithium soap; heating the mixture carefully (due to foaming) to eliminate the water until it is uniform at a temperature from about 350° F. to 430° F.; rapidly cooling the mixture to about 300° F. or below by quenching with additional lubricating oil and finally incorporating the remainder of the lubricating oil into the grease composition. The lithium soap or complex was prepared in situ and not isolated.

SUMMARY OF THE INVENTION

The invention relates to the preparation of lithium carboxylates having at least four carbon atoms in a process whereby the product can be recovered without filtration.

According to the process, either solid or molten carboxylic acid or glyceride thereof having at least four carbon atoms is added to a heated reaction vessel with high shear stirring. A stoichoiometric amount of lithium hydroxide monohydrate crystals or a concentrated solution thereof is added with heating and stirring. The heating and stirring is continued until the reaction is complete and the water driven off and the product is essentially dry.

The resulting product can be used in the manufacture of compositions containing lithium carboxylates such as soaps, oils and greases.

One or more monobasic or polybasic acids can be utilized.

It is therefore a general object of the invention to provide a process for preparing lithium carboxylates without requiring a filtration step.

It is a further object of the invention to provide lithium carboxylates salts or soaps thereof which can be used to prepare additives, oils or greases.

DESCRIPTION OF THE PREFERRED EMBODIMENTS

According to the invention lithium carboxylates having at least four carbon atoms can be prepared in a dry powder form without the requirement of filtration or expensive separation so as to be useful in oils, soaps and greases. The preparation is carried out using the acids or glyceride esters of the acids including mixed mono-, di- and triglyceride esters derived from animal fats, and oils and/or vegetable fats and oils. Such materials comprise fatty acid esters having 10 to 20 carbon atoms and are well known for use in soap making processes.

By "glycerides" herein is meant organic acid esters of glycerol. The term "glycerides" encompasses mono-, di- and triglycerides, since glycerol is a trihydric alcohol which can be esterfied on any, or all, of the three hydroxyl groups. Triglycerides constitute the major components of naturally occurring fats and oils which are typically used as starting materials in soap making processes.

By "animal or vegetable fats and oils" herein is meant the organic acid glyceride materials which can be secured from a wide variety of sources. Specific, non-limiting examples of such materials include lard, tallow, coconut oil, palm oil, various by-products from animal rendering operations, oils from oleaginous seeds such as the soybean, sunflower seeds, and the like, cottonseed oil, etc. Typical listings of such materials are widely available, and all such glyceride mixtures are useful in the present process.

It has also been found that one can efficiently react a carboxylic acid or dicarboxylic acid or a mixture thereof, for example, 12-hydroxystearic acid directly with lithium hydroxide in a reactor equipped with high shear stirrers which stir the entire contents of the reactor. This is accomplished by adding a concentrated lithium hydroxide solution (preferably saturated to reduce the amount of water), or even lithium hydroxide monohydrate with essentially no oil present. The oil slows down the reaction and produces foam and ultimately a paste. In fact it has been found that a coarse to fine powder is produced upon complete reaction and removing substantially all of the water. this performed lithium ester powder can be conveniently discharged from the reactor and shipped to another location and incorporated into a grease formulation to produce a satisfactory lithium grease equivalent to that which is made by reacting the same carboxylic acid in situ with the lithium hydroxide in the base oil. This avoids the 3 to 4 hour reaction time normally required for the lithium hydroxide to react with 12-hydroxystearic acid (HSA) or hydrogenated castor oil (HCO) in the presence of base oil and this avoids controlling the foaming due to water which must be removed.

Crystalline $LiOH.H_2O$ and HSA can be reacted together starting at room temperature and the temperature taken up to 110° C. and held for 15 to 30 minutes with good stirring. A saturated aqueous solution of LiOH (about 10.8%) can be added directly to molten HSA at 100–120° C. to form the desired lithium 12-hydroxy stearate (LHS). The conditions can be varied over a wide range. The key is to react the HSA molten (above 86° C.) with lithium hydroxide with the amount of water ranging from the monohydrate up to a 5% by weight LiOH solution with essentially no oil present (less than 30% by weight of the HSA). After the reaction is complete, up to 10% oil can be added to control dustiness and yet retain good flowability.

In the case of hydrogenated castor oil (HCO), the saponification of this triglyceride also proceeds as almost readily as the reaction with the HSA in the above described processes and produces the same resulting lithium 12-hydroxystearate which contains about 8% glycerine which is also formed in the saponification. This material can be used directly in making lithium greases which currently use HCO.

The preferred process conditions for making the lithium salts of carboxylic and polycarboxylic acids containing 4 or more carbon atoms including HSA, HCO and other triglycerides and mixtures thereof is the following:

a) Charge the stirred reactor with the requisite amount of acid or triglyceride material and heat up to 100–110° C.;
b) Add the stoichiometric amount of a freshly filtered saturated lithium hydroxide solution (about 10.8% by weight) slowly over 30 minutes while maintaining the temperature between 90 and 110° C. Stir and continue heating to drive off the water at 100–120° C. Vacuum can be applied to assist and speed up the removal of the water. Vigorous stirring is maintained throughout this entire sequence. The mixture becomes very doughy just after neutralization is complete and remains this way until about half the water is removed. It then changed slowly into a powder on further drying.
c) The powder after total water removal is then cooled and discharged into a shipping container.

The product should be less than 0.5% water. The product may be adjusted to neutral to slightly acid or even slightly basic during the neutralization step depending on the grease formulation for which it is to be used. The yield is quantitative. The handling has been minimized in this process and the water removal step has been optimized using the least amount that is practicable. The present process avoids the use of a filtration or spray drying step which is time consuming and messy with these wax-like products.

Certain lubricant manufacturing operations require a preformed lithium soap such as synthetic lubricants used in aircraft since their base stock oils are high molecular weight esters or organic phosphates which can not tolerate the presence of lithium hydroxide. Therefore the lithium soap must be preformed.

In the case of lithium complex greases, these are complex mixtures of lithium 12-hydroxystearate and a dibasic acid such as azelaic acid, sebacic acid, succinic acid, etc., which are made in the grease all together. The ratio of HSA to azelaic acid or other dibasic acid weight ratio in these complex greases is usually 3/1 to 0.5/1 by weight. These complex lithium salts have never been preformed and dried before. It has been found that these complexes do form and separately, the corresponding lithium salts of the dibasic acids alone, can both be readily made by the present process. These preformed complexes readily form a satisfactory lithium complex grease.

The following examples illustrate the practice of the invention, but are not intended to be limiting thereof.

Comparative Example 1
Preparation of Lithium Carboxylates 523 g. of 12-hydroxystearic acid (HSA) (from hydrogenated castor oil) is added to 2500 ml water in a 5-1 flask and heated to above 90° C. with stirring. The contents formed a creamy emulsion. At this point there was added 373 g saturated LiOH solution (10.8% by weight) over 45 minutes. The mixture was stirred another 15 minutes and cooled. The very thick slurry, which formed, had a pH of 7–8 and was filtered using vacuum/pressure filtration with difficulty. The damp pressed solid was finally dried in a vacuum desiccator at 110° C. for 5 hr. The yield was 490 g. of dry grainy lithium 12-hyroxystearate.

Comparative Example 2

522 g. of 12-hydroxystearic acid (from hydrogenated castor oil) was added to 1500 ml water in a 5-1 flask and heated to above 90° with stirring. The contents formed a creamy emulsion. At this point there was added 405 g. of saturated LiOH solution (10.8% by weight) over 1.5 hrs. The mixture was stirred another 15 minutes and cooled. The very thick slurry of lithium 12-hydroxystearate had a pH of 9–10 and would not filter readily.

EXAMPLE 1

100 g of molten 12-hydroxystearic acid (HSA) (about 100° C.) and 80 g of conc. LiOH solution (10.8%) was simultaneously added to a heated stainless steel beaker with a high shear stirrer. The reaction was instantaneous and everything turned to a waxy solid. The stirrer and further heating caused the waxy solid to form a powder which give off steam as it dried while being stirred. The sample was dried for an hour under vacuum to be sure that it was dry. Yield of lithium 12-hydroxstearate was 100 g, (99%).

EXAMPLE 2

372 g. of molten 12-hydroxystearic acid (about 115° C.) and 480 g. of conc. LiOH solution (6.3%) were simultaneously added to a heated stainless steel beaker with a high shear stirrer. The reaction was instantaneous and everything turned to dough consistency. The sample was dried for an hour under vacuum @ 100° C. pH of solid was 7–8. Yield of lithium 12-hydroxystearate powder was 320 g. (91%).

EXAMPLE 3
Preparation of a Complex

A hot mixture of 200 g HSA and 100 g of azelaic acid were added to a heated stainless steel bowl of a heavy duty laboratory size mixer (Kitchen Aid 4.5-liter size) and 390 g. (10.8% saturated) LiOH solution were added over about 5 minutes. A temperature of above 80° C. was maintained for 30 minutes. The material had a pH of 8–9. The reaction ran very quickly and material behaved like a coarse lumpy powder. The 2:1 complex was dried at 100° C. for 4 hours under vacuum. The product was ground in a blender to give a very fine powder. The yield of lithium 12-hydroxystearate/ dilithium azelate was 243 g.

EXAMPLE 4

250 g. of hot castor oil (about 115°) and 32 g of light viscosity mineral oil was added to a heated stainless steel bowl of a heavy duty laboratory size mixer (Kitchen Aid) with a high shear stirrer. Then 236 g. of LiOH solution (10.8%) was added to the molten HSA. The reaction was rapid and everything turned to powder consistency. The oil kept the powder from being dusty The pH of the solid was 8. The sample was dried under vacuum for 2 hrs @ 100° C. The pH of the solid was 7–8. Yield of lithium 12-hydroxystearate nondusting powder was 335 g. (95%).

EXAMPLE 5
Formation of Complex 1100 g. of HSA was added and heated in a stainless steel bowl with a heavy duty laboratory size mixer (Kitchen Aid 4.5-1 size) to 110° C. and then added 400 g. of azelaic acid (Henkel #1440 was added). The mixture was stirred and heated until dissolved at 110° C. The 1600 g. of saturated LiOH solution (10.8%) was added over about 45 minutes. A temperature of 85–90° C. was maintained for 45 minutes and cooled. The material had a pH of 8. The material was ran through a blender to ensure the finest material available. The 2.75:1 complex was dried at 100° C. for 4 hours under vacuum. The coarse powder product was ground in a blender to give a very fine powder. The yield of lithium 12-hydroxystearate/dilithium azelate was 1550 g.

EXAMPLE 6

300 g. of molten HSA (about 115° C.) and 230 g of LiOH solution (10.8%) were added to a heated stainless steel bowl of a heavy duty laboratory size mixer (Kitchen Aid) with a high shear stirrer. Then 210 g of light viscosity mineral oil (60%) was added to the reaction mixture. The reaction was rapid and everything turned to a butter-like consistency. The oil kept the powder from being dusty and the product was better at blending into a grease formulation. The pH of the solid was 8. The sample was dried under vacuum for 2 hrs. @ 100° C. The pH of the solid was dried under vacuum for 2 hrs. @ 100° C. The pH of the solid was 7–8. Yield of lithium 12-hydroxstearate nondusting (41%) waxy powder was 510 g. (95%).

EXAMPLE 7

200 g. of hot molten 12-hydroxystearate (110° C.) was added to a heated stainless steel bowl of a heavy duty laboratory size mixer (Kitchen Aid). The bowl was heated with stirring with a reaction mixture and was maintained about 95–100° C. for 60 minutes and had a very thick doughy consistency. The mixture was dried in vacuum dessicator for 4 hours at 100° C. The yield of lithium 12-hydroxystearate powder was 190 g. (95%).

EXAMPLE 8

Preparation of Grease 30 g. of the product of Example 9 was added to 170 g. of Chemtool HC-750 oil which had been heated to 95° C. The slurry was heated while slowly stirring. The light powder dispersed very readily into the oil at 105° C. and was almost completely dissolved at 130° C. At 200° C. the entire solution began to liquefy and formed an opaque solution at 220° C. at which point it was cooled. The material was crumbly at room temperature, but it was then homogenized to form a very smooth, thick grease (an NGLI #4 grad).

Worked Penetration=195

Dropping Point=415° F.

This indicates that this thickener system needs far less than 15% of this complex to form a good NGLI #4 grease.

EXAMPLE 9

To 179.45 grams of Chemtool HC-750 of oil that was heated to 95 degrees C., 18.05 grams of the product of Example 1 were added. This material dispersed readily in the oil, and it formed an opaque solution. When stirring was stopped for a short time, the material seemed to settle to the bottom readily. Stirring and heating were continued and at 160 degrees C., the solution began to thicken. It was still thick, but somewhat fluid, at 175 degrees C. At 180 degrees C., the solution began to form a grease structure, and then as the temperature was increased to 190 degrees C., the solution began to thin out. At 200 degrees C., the soap had completely dissolved in the oil, forming a clear oil solution. Heat was removed, and when the batch had cooled to room temperature, it was homogenized in a Morehouse laboratory mill. The properties for this sample were:

Worked penetration=255

Dropping point=394 degrees F.

EXAMPLE 10

179.45 grams of Chemtool HC-750 oil was heated to 95 degrees C. and then added 18.05 grams of the product of Example 2. It dispersed readily into the oil, and then began to thicken the oil slightly at 170 degrees C. It slowly completely dissolved before reaching 200 degrees C., forming a clear light brown oil solution. Heat was removed allowing the batch to cool to room temperature. It was homogenized in the Morehouse laboratory mill. The smooth grease had the following properties:

Worked penetration=299

Dropping point=399 degrees F.

What is claimed is:

1. A process for the preparation of lithium carboxylate compounds of four or more carbon atoms and recovering the product without filtration which comprises the steps of:

a) adding at least one molten carboxylic acid or glyceride ester thereof having at least four carbon atoms to a heated reaction vessel with high shear stirring;

b) adding the requisite amount of concentrated lithium hydroxide aqueous solution or lithium hydroxide monohydrate crystals;

c) heating the stirred mixture to a temperature of at least 80° C., and then;

d) heating and stirring the resulting lithium carboxylate mixture until dry.

2. The process of claim 1 whereby said glyceride ester is a triglyceride.

3. The process of claim 1 whereby said carboxylic acid is a mixture of acids.

4. The process of claim 1 whereby said carboxylic acid is a polybasic acid.

5. The process of claim 1 whereby said carboxylic acid is a mixture of a monobasic and a polybasic acid.

6. The process of claim 1 wherein lithium hydroxide monohydrate is used.

7. A process of claim 1 wherein said carboxylic acid is 12-hydroxystearic acid.

8. A process for manufacturing lithium carboxylate compounds of four or more carbon atoms which comprise the following steps:

a) adding at least one molten carboxylic acid or glyceride ester thereof having at least four carbon atoms to a reactor with high shear stirring and heating to a temperature of a least 80° C.;

b) adding a stoichiometric amount of lithium hydroxide as monohydrate crystals or concentrated solutions thereof;

c) heating the stirred mixture above 80° until reacted; and then d) heating and stirring the resulting lithium carboxylate mixture until dry.

9. The process of claim 8 wherein said glyceride is a triglyceride.

* * * * *